(12) United States Patent
Telischak et al.

(10) Patent No.: US 7,996,068 B2
(45) Date of Patent: Aug. 9, 2011

(54) SURGICAL METHOD AND APPARATUS FOR IDENTIFICATION OF FLUORESCENCE

(75) Inventors: Nicholas Alexander Telischak, Belvedere, CA (US); Brett Matthew Wingeier, San Francisco, CA (US); Alissa Erin Murphy, Palo Alto, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 708 days.

(21) Appl. No.: 11/959,367

(22) Filed: Dec. 18, 2007

(65) Prior Publication Data

US 2009/0054767 A1 Feb. 26, 2009

Related U.S. Application Data

(60) Provisional application No. 60/942,246, filed on Jun. 6, 2007, provisional application No. 60/894,703, filed on Mar. 14, 2007.

(51) Int. Cl.
*A61B 6/00* (2006.01)

(52) U.S. Cl. .......................... 600/476; 600/431

(58) Field of Classification Search .................. 600/431, 600/473, 476, 478; 356/39–42, 302, 326, 356/610, 615, 628–629, 931
See application file for complete search history.

(56) References Cited

U.S. PATENT DOCUMENTS

| | | | |
|---|---|---|---|
| 4,541,438 A | 9/1985 | Parker et al. | |
| 4,821,117 A | 4/1989 | Sekiguchi | |
| 4,981,138 A * | 1/1991 | Deckelbaum et al. | 600/477 |
| 5,749,830 A | 5/1998 | Kaneko et al. | |
| 5,769,791 A * | 6/1998 | Benaron et al. | 600/473 |
| 5,807,261 A * | 9/1998 | Benaron et al. | 600/473 |
| 5,910,816 A | 6/1999 | Fontenot et al. | |
| 6,110,106 A * | 8/2000 | MacKinnon et al. | 600/181 |
| 6,185,443 B1 * | 2/2001 | Crowley | 600/407 |
| 6,440,389 B1 | 8/2002 | Rabito | |
| 6,477,403 B1 * | 11/2002 | Eguchi et al. | 600/478 |
| 6,503,195 B1 * | 1/2003 | Keller et al. | 600/160 |
| 6,748,259 B1 | 6/2004 | Benaron et al. | |
| 6,863,650 B1 | 3/2005 | Irion | |
| 6,962,690 B2 | 11/2005 | Kiefer et al. | |

(Continued)

OTHER PUBLICATIONS

Stiles, B.M., et al., "Fluorescent cholangiography in a mouse model: an innovative method for improved laparoscopic identification of the biliary anatomy", Surgical Endoscopy, 2006, 20:1291-1995.

(Continued)

*Primary Examiner* — Francis Jaworski
(74) *Attorney, Agent, or Firm* — Bozicevic, Field & Francis LLP; Bret E. Field; Lynn J. Kidder

(57) ABSTRACT

Devices and methods for use in detecting an optical signal, such as from a fluorescent agent, and converting it to a visible signal are provided. Aspects of the devices include a first light source that emits light onto a region of interest such as a body tissue, body fluid, or agent such as a fluorescent agent introduced into the body; a detector for detecting light emitted or reflected from the region of interest; and a visible light source that emits visible light onto the region of interest, where the color or intensity of the visible light is selected based on the amount of light at one or more wavelengths detected by the detector. Devices and methods of the invention find use in a variety of applications, such as in applications in which it is desired to identify an anatomical structure during surgery, without the need to eliminate ambient light.

22 Claims, 5 Drawing Sheets

U.S. PATENT DOCUMENTS

| | | | |
|---|---|---|---|
| 7,258,663 | B2 | 8/2007 | Doguchi et al. |
| 7,413,572 | B2 * | 8/2008 | Eimerl et al. ............... 607/88 |
| 7,583,993 | B2 * | 9/2009 | Sendai ........................ 600/476 |
| 7,677,737 | B2 * | 3/2010 | Lonn ............................. 353/69 |
| 7,728,868 | B2 * | 6/2010 | Razzaque et al. ............ 348/77 |
| 7,818,042 | B2 * | 10/2010 | Granger ..................... 600/407 |
| 7,846,091 | B2 * | 12/2010 | Fulghum ..................... 600/160 |
| 2005/0143662 | A1 * | 6/2005 | Marchitto et al. ........... 600/473 |
| 2006/0239921 | A1 | 10/2006 | Mangat et al. |
| 2008/0004525 | A1 * | 1/2008 | Goldman et al. ............ 600/425 |
| 2008/0027317 | A1 * | 1/2008 | Wood et al. .................. 600/427 |
| 2008/0103390 | A1 * | 5/2008 | Contag et al. ................ 600/427 |

OTHER PUBLICATIONS

Tulikangas, Paul K., et al., "Assessment of laparoscopic injuries by three methods", Fertility and Sterility, Oct. 2001, vol. 26, No. 4, pp. 817-819.

Holzinger, F., et al., "Use of a fluorescent bile acid to enhance visualization of the biliary tract and bile leaks during laparoscopic surgery in rabbits", Surgical Endoscopy, 2001, 15: 209-212.

Oddi, A., et al., "Intraoperative Biliary Tree Imagining with Cholyl-Lysyl-Fluorescein: An Experimental Study in the Rabbit", Surgical Laparoscopy & Endoscopy, 1996, vol. 6, No. 3, pp. 198-200.

McHutchison, Lynda L. Burt, et al., "Preservation of ovarian tissue in adnexal torsion with fluorescein", Am J Obstet Gynecol, May 1993, vol. 168, No. 5, pp. 1386-1388.

Holmes, Nathaniel J., et al., "Intraoperative Assessment of Bowel Viability", Journal of Investigative Surgery, 1993, vol. 6, pp. 211-221.

Bergman, R. Thomas, et al, "The Role of Intravenous Fluorescein in the Detection of Colon Ischemia During Aortic Reconstruction", Annals of Vascular Surgery, 1992, vol. 6, No. 1, pp. 74-79.

Udshmadshuridze, Von N. S., et al, "Intraoperative Harnleiterdarstellung mit Fluoreszein-Natrium", Z Urol. Nephrol, 1988, 81: 635-639.

* cited by examiner

US 7,996,068 B2

SURGICAL METHOD AND APPARATUS FOR IDENTIFICATION OF FLUORESCENCE

CROSS-REFERENCE TO RELATED APPLICATIONS

Pursuant to 35 U.S.C. §119 (e), this application claims priority to the filing date of the U.S. Provisional Patent Application Ser. No. 60/942,246 filed Jun. 6, 2007 and to the filing date of U.S. Provisional Application Ser. No. 60/894,703 filed Mar. 14, 2007; the disclosures of which applications are herein incorporated by reference.

INTRODUCTION

Abdominal and pelvic anatomy is complex, and there are many operations and procedures in which the location of delicate anatomical structures is important for the prevention of injury to those structures. For example, the location of the ureters which connect the kidneys to the bladder makes them difficult to identify during abdominal and pelvic surgery. A ureter may be inadvertently injured during open surgery or laparoscopy, which can lead to significant human, economic, and legal costs. It is estimated that the incidence of ureteral injury during any abdominal or pelvic operation is between 0.5-2.0%. An increase in the incidence of ureteral damage may also be related to an increase in the number of laparoscopic procedures. The average cost of ureter repair is $50,000 per ureteral injury. Similarly, locating the bile ducts is important to avoid injury during open or laparoscopic cholecystectomies. It is estimated that the incidence of bile duct injury during laparoscopic cholecystectomies is 0.4-0.6%, with the average cost of $20,000-$130,000 per bile duct injury.

An effective and universally adopted method to better identify anatomical structures such as the ureters during pelvic and abdominal surgery would have the potential to prevent more than 5,000 ureteral injuries a year. When ureters are injured, the outcome is dependent on the extent of the injury as well as how quickly it is discovered. Permanent damage can usually be avoided if the diagnosis of the ureteral injury is made at the time of surgery. However, between 8-57% of all ureteral injuries are recognized not intra-operatively but post-operatively. Delay in diagnosis can result in ureteral fistula, urinoma, infection, hydronephrosis, and loss of renal function.

Most authors have concluded that the key to prevention of ureteral injury is identification and protection of the ureters. For open surgical procedures, exposure of a wide operative field, attention to ureteral vascular supply, methodical control of bleeding, and surgical skill are important. Unfortunately, a wide operative field is not conducive to rapid healing and a short hospital stay, nor is it possible with laparoscopic procedures. Similarly, a wide operative field is not possible in most cholecystectomies, given the increasing trend toward laparoscopic cholecystectomies.

Therefore, there is considerable interest in the development of new techniques for use in both open and minimally invasive procedures that address the problems of locating anatomical structures such as the ureters or bile ducts during abdominal and pelvic surgery.

SUMMARY

Devices and methods for use in detecting an optical signal, such as from a fluorescent agent under normal ambient light during surgery, are provided. Aspects of the devices include a first light source that emits light onto a region of interest such as a body tissue, body fluid, or agent such as a fluorescent agent introduced into the body; a light detector for detecting light emitted or reflected from the body tissue, body fluid, or introduced agent; and a visible light source configured to emit visible light onto the body tissue, body fluid, or introduced agent where the visible light has a color or intensity that is selected based on the amount of light detected by the detector at one or more wavelengths of interest. The one or more wavelengths detected may be selected depending on the application to be characteristic of the introduced agent, the body tissue, or a physiological parameter related to the body tissue. The device may be a hand-held device or a percutaneous device.

Devices and methods of the invention find use in a variety of applications, such as in applications in which it is desired to identify an anatomical structure during surgery, without the need to eliminate ambient light. The devices and methods of the invention can also be used in applications such as Optical Intrinsic Signal (OIS) mapping where measurement of a physiological parameter is desired, such as hemoglobin concentration or oxygenation, and can be determined by detecting scattered light at particular wavelengths from a region of interest.

DETAILED DESCRIPTION

Figure 1:
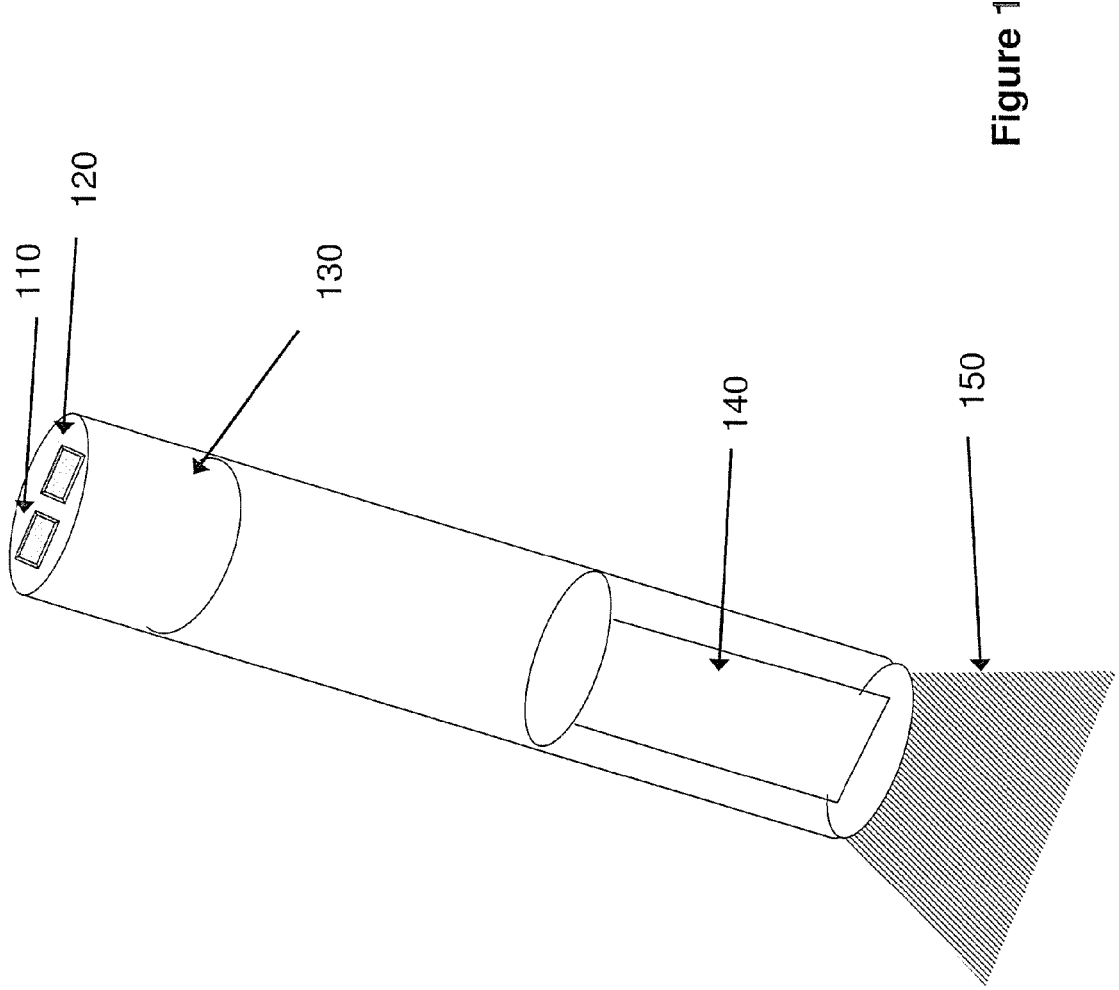
FIG. 1 provides a view of the device in accordance with an embodiment of the invention.

Devices and methods for use in detecting an optical signal, such as from a fluorescent agent under normal ambient light during surgery, are provided. Aspects of the devices include a first light source that emits light onto a region of interest such as a body tissue, body fluid, or agent such as a fluorescent agent introduced into the body; a detector for detecting light emitted or reflected from the body tissue, body fluid, or introduced agent; and a source of visible light that emits visible light onto the body tissue, body fluid, or introduced agent where the visible light has a color or intensity that is selected based on the amount of light at one or more wavelengths detected by the detector. The one or more wavelengths detected may be selected depending on the application to be characteristic of the introduced agent, the body tissue, or a physiological parameter related to the body tissue. The device may be a hand-held device or a percutaneous device.

Devices and methods of the invention find use in a variety of applications, such as in applications in which it is desired to identify an anatomical structure during surgery, without the need to eliminate ambient light. The devices and methods of the invention can also be used in applications such as Optical Intrinsic Signal (OIS) mapping where measurement of a physiological parameter is desired, such as hemoglobin concentration or oxygenation, and can be determined by detecting scattered light at particular wavelengths from a region of interest.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

Any recited method can be carried out in the order of events recited or in any other order which is logically possible.

Devices

As summarized above, the subject devices are devices that find use in detecting characteristic wavelengths of light emitted or reflected by body tissue, body fluid, or agents introduced into the body in a region of interest during therapeutic or diagnostic procedures such as surgery, and then converting the optical signal from the detected wavelengths into visible light that is projected back onto the region of interest. As such, devices of the invention can be used to 'translate' an optical signal, such as from a fluorescent agent, that is normally 'invisible' under ambient light conditions into a visible light that is projected back onto the region of interest. For example, devices of the invention can be used to locate an anatomical structure in the body during surgery. Devices of the invention can also be used to locate pathological body tissue or body fluid, and can be used to locate or measure the amount or concentration of an introduced agent present in a region of interest (e.g., a fluorescent agent). Devices and methods of the invention can be used to measure a physiological parameter within the field of view of the device's first light source and light detector. For example, the device can be used for detection of physiological parameters like blood perfusion, by looking at the isosbestic wavelengths of hemoglobin which reflects hemoglobin concentration, or can be used to measure oxygenation vs. deoxygenation of hemoglobin, e.g., by detecting wavelengths in the 600-650 nm range, etc.

Embodiments of the device include both hand-held and percutaneous configurations (e.g., for use in laparoscopic or endoscopic procedures). In some embodiments, the devices can be disposable. In some embodiments, the devices can be reusable.

Devices of the invention are structures that have a first light source that emits light onto a region of interest, e.g., for excitation of a fluorescent agent, a light detector that detects light, and a visible light source configured to emit visible light onto the region of interest having a color that is selected based on the amount of light detected by the light detector. In some embodiments, the visible light source is configured to emit visible light onto the region of interest having an intensity that is selected based on the amount of light detected by the light detector. The visible light can be projected directly back onto the tissue, in the same region of interest where the first light source is projected. In this manner the device can provide a method of 'translating' the optical signal from a fluorescent agent, or the optical signal from reflected light such as with optical intrinsic signal (OIS) mapping, which can be invisible under normal ambient light conditions, to a clear visible signal which can be projected onto the operative or therapeutic field.

In describing the subject devices, the proximal end of the hand-held device for use in open procedures is defined as the end of the device that is closest to the operator of the device i.e., the end of the device that is furthest away from the body during use. The proximal end of the percutaneous device is further defined as the end of the device that is not inside the animal body during use, i.e., the end that is most distant or furthest away from the end of the device that is inside of the body during use. In other words, the proximal end of the device is the end of the device that is outside of the body during use.

In contrast, the distal end of the hand-held device is the end of the device that is closest to the body during use, i.e., the end that is furthest from the operator of the device. The distal end of the device is the end at which at least one light source is located, where this feature is further described below. The distal end of the percutaneous device is defined as the portion of the device that is placed inside of the body during use, and the end at which at least one light source is located.

For percutaneous devices according to embodiments of the invention, the proximal and distal ends are separated by an elongated tubular portion, with a distance or length sufficient to provide for the proximal end to be outside of the body and the distal end to be inside of the body during use. As such, the distance between the proximal and distal ends in embodiments of the subject invention may be of any length as is commonly found in endoscopic or other percutaneous devices. The length may range from 7 to 200 centimeters, such as from 25 to 130 and including from 30 to 120 centimeters. Depending on the particular application for which the device is intended to be employed, the body of the device may be rigid or flexible. Where the body is rigid, e.g., as would be found in a device designed for use in laparoscopic or other trocar sleeve accessed surgical procedures, the distance between the proximal and distal ends may range from 7 to 50, such as from 25 to 45 and including from 30 to 40 centimeters. In those embodiments where the body of the device is flexible, e.g., in endoscopic embodiments of the subject invention where the device is to be used to access through a tortuous or at least curvilinear pathway, the distance between the proximal and distal ends may range from about 7 to 200, such as from 25 to 175 and including from about 50 to 125 centimeters.

Additionally, the device can also be dimensioned for inclusion with or adapted onto an endoscopic device, such that it can be incorporated with or used in combination with the optical system of an endoscope, or in some embodiments the device can be used as the optical system for an endoscope, for example.

For hand-held devices according to embodiments of the invention, the proximal and distal ends are separated by an elongated tubular portion with a distance or length sufficient to provide for inclusion of the component parts of the device (e.g., the processor, batteries), such that in one embodiment the device is of a size that can be conveniently held in one hand. By "hand-held" is meant a device that is portable, and in some embodiments is a device that is of a size that can be conveniently held in one hand. However a "hand-held" device may also include embodiments where the device is held on a stand, or other positioning device, or with securing means such that the device is held in position in such a way as to be directed to the area of interest of the surgical or procedural field. In some embodiments the "hand held" device can be a device that can be clipped or otherwise attached to an existing endoscopic tool, or to any other tool such as a stapler, or to an existing light source. The distance between the proximal and distal ends ranges in certain embodiments from 7 to 50 centimeters, such as from 10 to 30 and including from about 12 to 20 centimeters.

Located at the distal end of the device is at least one light source that emits light at a first wavelength. In certain embodiments, the device has a plurality of light sources that emit light at a first wavelength (210 in FIG. 2). By plurality is meant 2 or more, where the number may range from 2 to 12, such as 6 to 10, e.g., 8. In certain embodiments, the light source can be a light-emitting diode (LED). In some embodiments, the first light source is a collimated light source. In some embodiments, the light source can be any other light source suitable for optical intrinsic signal (OIS) spectroscopy or excitation of fluorescence, such as lasers, photodiodes, and lamps, including mercury or xenon lamps, a flash lamp, or incandescent bulb. The light source can be a continuous or pulsed light source. For example, a device can emit light at an isosbestic wavelength of hemoglobin such as 525 nm, and can also emit light at a wavelength such as 625 nm, and by measuring the amount and type of reflected light a parameter such as blood oxygenation can be determined. The device can then reproject its visible light spot, which can have a color which is based on this measured parameter.

During use, the light source can emit light in a first wavelength suitable for the excitation of fluorescence. The light source can also emit light in a first wavelength suitable for optical intrinsic signal spectroscopy (OIS). The first light source can emit light at one or more wavelengths. The first wavelength can be a wavelength in the ultraviolet, visible light, or infrared spectrum. The light source can therefore emit light at a wavelength ranging from 1 nm to 350 µm, such as from about 300 nm to 750 nm, including from about 350 nm to 495 nm.

The light detector is also located at the distal end of the device. The light detector can be any suitable detector, e.g., a phototransistor or photodiode. In some embodiments, the device has more than one light detector. In some embodiments, the device may have two, three, four, or more light detectors. The light detector can be a detector that detects light at primarily one wavelength, or it can be a detector that can detect the light at one or more wavelengths, e.g., a multichannel detector. The light detector can be made of any material suitable for producing photocurrents for the wavelength or wavelengths of interest. Materials can include but are not limited to silicon, germanium, indium gallium arsenide, or lead sulfide. In some embodiments, the light detector detects light at a wavelength ranging from 1 nm to 350 µm, such as from 300 nm to 750 nm, including from 500 to 530 nm, e.g., 521 nm (the emission wavelength of fluorescein).

The device can also include one or more optical filters at the distal end. The one or more optical filters can be any suitable optical filter. The optical filter or filters can be placed such that the light reflected from the region of interest, or from the fluorescent agent, passes through the optical filter before reaching the light detector. The one or more optical filters may be constructed to preferentially transmit the one or more wavelengths of interest.

Located at the distal end of the device is at least one source of visible light. By "visible light source" is meant one or more sources of light, e.g., a diode or laser, than can project light in the visible range. In certain embodiments, the visible light source includes a diode. In some embodiments, the visible light source comprises a first diode and a second diode. In some embodiments, the visible light source comprises more than two diodes, such as three or more, or four or more diodes.

In some embodiments, the first diode can emit light at a wavelength that is in the "green" range of the color spectrum, such that the wavelength ranges from 495-570 nm, such as from 500 to 550 nm, e.g., 520 nm. In some embodiments the second diode can emit light at a wavelength that is in the "red" range of the color spectrum, such that the wavelength ranges from 620 to 750 nm, such as from 630 to 700 nm, e.g., 650 nm. The first, second, or any additional diodes can emit visible light at a wavelength of any color in the visible spectrum, ranging from 400 nm to 750 nm, such as from 410 nm to 700 nm.

The color of the visible light that is projected from the device can be selected based on the amount of light detected by the light detector, at the wavelength or wavelengths of interest for detection. The overall intensity of the visible light that is projected from the device can also be selected based on the amount of light detected by the light detector, at the wavelength or wavelengths of interest for detection. By "intensity" is meant the "brightness" or "strength" of the light; or the perception of the amount of light that a given source appears to emit.

Figure 5:
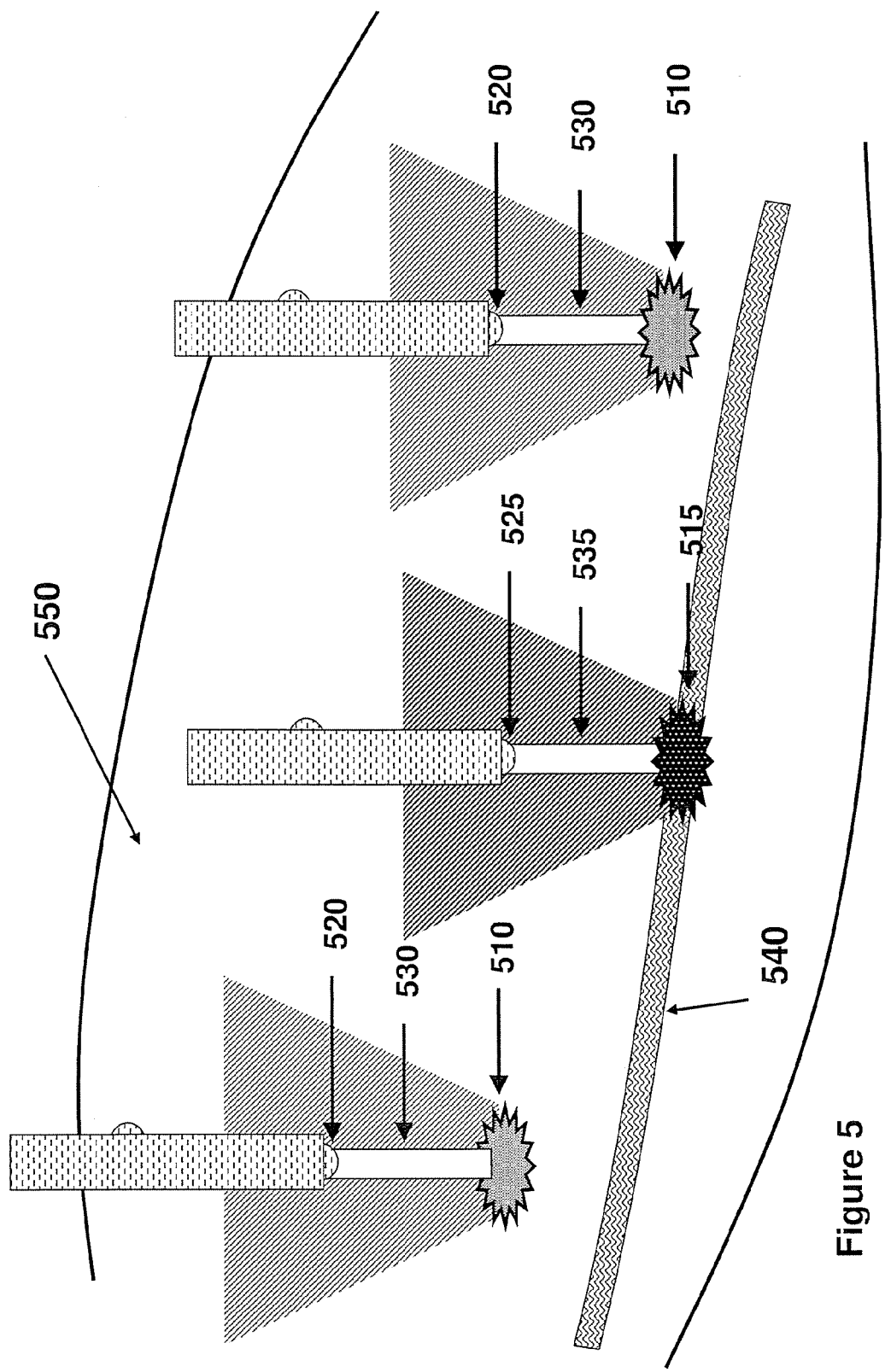
FIG. 5 illustrates use of a device in accordance with an embodiment of the invention to locate a ureter during surgery.

By "visible light" is meant the light that is projected from the distal end of the device that is in the visible spectrum of wavelengths, of sufficient intensity or strength to be perceived by the unaided human eye under ambient light conditions. For example, light that is projected back onto the operative field, as shown in FIG. 5. In some embodiments the "visible light" comprises a single visible light source (e.g., a red diode); in other embodiments the "visible light" comprises two light sources (e.g., a red diode and a green diode), and as such, the color of the "visible light" that is projected is a blend of the colors of the individual "visible light sources" employed (e.g., the resultant blend of red and green can be yellow light). As an example, the visible light source can include a green diode and a red diode, and the fluorescent agent can be fluorescein. If no fluorescein is detected by the light detector (e.g., a phototransistor), the color of the visible light that is projected can be green. If a significant amount of fluorescein is detected, the color of the visible light that is projected can be red. If the amount of fluorescein detected is greater than zero, but less than a predetermined threshold amount, the color of the visible light that is projected can be a mixture of the light from the green diode and the red diode, e.g., a yellow or orange color. The visible light source can therefore have a color ranging from green to red. In this manner, the amount of detected fluorescence which is normally not visible with ambient room lights can be 'translated' into visible light that can be projected onto a surgical field, for example.

In some embodiments, the "visible light" emitted onto the region of interest can be one or more light sources that have an intensity that is selected based on the amount of light detected by the light detector. As an example, the visible light source can be a red diode, and the fluorescent agent can be fluorescein. If no fluorescein is detected by the light detector (e.g., a phototransistor), the intensity of the visible light that is projected can be of a low intensity that is bright enough to be perceived by the unaided human eye. If a significant amount of fluorescein is detected, the intensity of the visible light that is projected can increase, so that the light is at a maximum brightness, or intensity. If the amount of fluorescein detected is greater than zero, but less than a predetermined threshold amount, the intensity of the visible light that is projected can be a medium intensity, that is an intermediate level of brightness between the low intensity and the maximum intensity. In this manner, the amount of the detected fluorescence which is normally not visible with ambient room lights can be 'translated' into visible light that can be projected onto a surgical field, for example.

By "optical signal" is meant any electromagnetic radiation that is emitted, reflected, or scattered after a light source, or electromagnetic radiation source, is emitted onto a region of interest. By "not visible" or "invisible" is meant an optical signal or other signal e.g., from a fluorescent agent, that either has a wavelength outside the visible light spectrum, or is a signal that cannot be seen by the unaided human eye under ambient light conditions, or is a signal that is substantially difficult to see with the unaided human eye under ambient light conditions.

The thresholds used for determining the amount of fluorescence needed to activate one or more visible light sources can be any suitable threshold that is found to be useful for a particular application. By "threshold" is meant an amount of fluorescence that will activate or deactivate a particular visual light source, e.g., a diode. One or more thresholds can be chosen such that at a particular level of light from an activated fluorescent agent that is detected by the light detector, the amount of current sent to a diode will change, e.g., increase or decrease, or the duty cycle of a diode will change, e.g., increase or decrease, such that the intensity of the light that is projected by that diode will increase or decrease, in proportion to the amount of fluorescence detected.

The intensity of each diode can therefore be controlled by either varying the duty cycle for each diode, or varying the current received by that diode. Any other suitable method for controlling the intensity of the visible light source can be used. For example, in the case of varying the duty cycle, when the light detector detects a low intensity of fluorescence, the duty cycle of the green diode increases, while that of the red diode decreases, and the user would perceive a green pointer, or green visible light. When the sensor detects a high intensity of fluorescence, the duty cycle of the red diode increases, and the user would perceive a red pointer, or red visible light. Thus, when moving the hand-held device from an area that is far from the anatomical structure of interest (e.g., ureter) to directly over a fluorescing structure or ureter, the user will see the output of visible color transition from green, to greenish-orange, to reddish-orange, to red. In this example, the projection of a green light not only indicates that the hand-held device is directed in an area far from the ureter, but can also confirm that the device is operational, by projecting a visible light at all times when the device is activated.

As discussed above, the thresholds can be experimentally determined such that the projected visible light can change from green to red, for example, a suitable distance from the anatomic structure of interest in order to provide the desired amount of accuracy for a particular application (e.g., the visible light changes to red when directly over the ureter; or the visible light changes to red when it is one centimeter from the ureter, etc.) Each device can be calibrated for the desired characteristics depending on the electrical and optical characteristics of the components used, as well as the anticipated application for the device. In some embodiments, the visible light is green when the amount of light detected at a second wavelength (e.g., the amount of fluorescence detected) ranges from 0 to 80% of the full dynamic range of the detector, such as from 5-75%. In some embodiments, the visible light is red when the amount of light detected at a second wavelength (e.g., the amount of fluorescence detected) ranges from 20% to 100% of the full dynamic range of the detector, such as from 25-95%. In some embodiments, the visible light is yellow-orange when the amount of light detected at a second wavelength (e.g., the amount of fluorescence detected) ranges from 10-90% of the full dynamic range of the detector, such as from 15-85%.

The color of the visible light projected serves as a visible signal indicating the proximity of an anatomical structure of interest. In some embodiments, the device can also include an additional indicator, e.g., a warning or alarm bell or signal.

In some embodiments of the invention, the devices and systems can include a processor (e.g., in the form of an integrated circuit or printed circuit board) that is present in the body of the device. As such, in certain embodiments the processor is configured to operate the subject device in a manner so that it operates as a "translator" of the signal from a fluorescent agent, which is not visually detectable under ambient light conditions, to a visible light that indicates the presence or absence of fluorescence, e.g., by having an appropriate control algorithm recorded onto a processor or control element of the device. By "translator" is meant that the device can detect light of one or more wavelengths that is reflected, scattered, or emitted from a region of interest, that may be undetectable with the unaided human eye under ambient light conditions, where the processor can convert the type and amount of detected light into a visible light of a particular color that is projected back onto the region of interest, thereby converting an 'invisible' light into a visible light. In certain embodiments the control element is configured to operate the device in a manner so that it operates as a detector of fluorescence, e.g., so that when no fluorescence is detected the visible light projected back onto the source region of interest is green, for example, and when a significant amount of fluorescence is detected the visible light projected back onto the source region of interest is red, for example.

In some embodiments the processor is configured to operate the subject device in a manner so that it operates as a "translator" of the one or more signals from a region of interest, which is not visually detectable by the unaided human eye, or is substantially difficult to see with the unaided human eye under ambient light conditions, to a visible light which has a color or intensity reflecting the result of the calculated physiologic parameter, such as hemoglobin concentration, by having an appropriate control algorithm recorded onto a processor or control element of the device. In some applications such as the measurement of, for example, blood oxygenation using the Beer-Lambert law from total and reduced hemoglobin measurements, the processor can perform calculations depending on the detected one or more wavelengths, and project a visible light which has a color reflecting the result of the calculated blood oxygenation measurement.

The energy source can be any suitable energy source, such as a battery. In some embodiments, the energy source is located at the opposite end from the light sources, e.g., the proximal end of the device. The energy source can also be a source of electricity, or can derive from a wireless source of energy. The proximal end can also include an on-off switch, which controls activation of the device, or one or more calibration controls, which allow the operator to adjust parameters affecting the initial excitation wavelength, as well as how the detected wavelength or wavelengths of light are translated into a visible-spectrum signal.

As mentioned above, the distal and proximal ends are generally separated by an elongated tubular member. While in many embodiments the cross-sectional shape of the member is most typically circular, other cross-sectional shapes are possible, e.g., square, rectangular, trapezoidal, triangular etc. The longest cross sectional dimension of the tubular elongate portion of the device may vary depending on the configuration of the device. In certain embodiments, this dimension ranges from 0.1 to 2.5, such as from 0.3 to 2.0 and including from 0.4 to 1.5 cm. In those embodiments of the device where the elongate member is flexible, e.g., in the endoscopic embodiments of the subject devices, the longest cross-sectional dimension of the elongate portion, e.g., the diameter of the tubular section, may be 0.1 cm or longer, such as 0.15 cm or longer and including 0.2 cm or longer, where the longest cross-sectional dimension may be as long as 2.0 cm or longer, but is 1.0 cm or shorter, including 0.75 cm or shorter in certain embodiments.

The individual elements of the subject devices may be fabricated from any convenient material, where at least the distal portion of the device and elements present at the distal portion, e.g., the first light source, the visible light source, etc., are ones that are fabricated from a biocompatible material. Biocompatible materials of interest include biocompatible polymers, where suitable biocompatible polymers include, but are not necessarily limited to: biocompatible polymers and/or elastomers. Suitable biocompatible polymers include, but are not necessarily limited to, materials such as, for example, polyethylene, homopolymers and copolymers of vinyl acetate such as ethylene vinyl acetate copolymer, polyvinylchlorides, homopolymers and copolymers of acrylates such as polypropylene, polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as polytetrafluoroethylene and polyvinyl fluoride, polystyrenes, homopolymers and copolymers of styrene acrylonitrile, cellulose acetate, homopolymers and copolymers of acrylonitrile butadiene styrene, polyvinylchloride, silicone rubber, polymethylpentene, polysulfones, polyesters, polyimides, polyisobutylene, polyetheretherketone, polymethylstyrene, and other similar compounds known to those skilled in the art. Suitable, biocompatible elastomers include, but are not necessarily limited to, biocompatible elastomers such as medical grade silicone rubbers, polyvinyl chloride elastomers, polyolefin homopolymeric and copolymeric elastomers, urethane-based elastomers, and natural rubber or other synthetic rubbers, fluorenated polymers (e.g., PTFE), and the like. In the catheter versions of the subject devices, the material from which the device is fabricated may include a radiodense material or some other imaging means to allow for visualization, e.g., with fluoroscopy. It should be understood that these possible biocompatible materials are included above for exemplary purposes and should not be construed as limiting.

The subject devices may be manufactured using any convenient protocol. Representative manufacturing methods that may be employed include machining, extrusion, and the like.

The description of the present invention is provided herein in certain instances with reference to a subject or patient. As used herein, the terms "subject" and "patient" refer to a living entity such as an animal. In certain embodiments, the animals are "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In certain embodiments, the subjects, e.g., patients, are humans.

FIG. 1 provides one embodiment of the device, which includes the processor (printed circuit board or PCB) 140 located at the distal end, and the batteries 130 and the on/off switch 110 located at the proximal end. In some embodiments there can also be one or more calibration controls 120, which allow the operator to adjust parameters affecting the initial excitation wavelength, as well as how the detected wavelength or wavelengths of light are translated into a visible-spectrum signal. Emitted light from the distal end is shown as 150.

Figure 2:
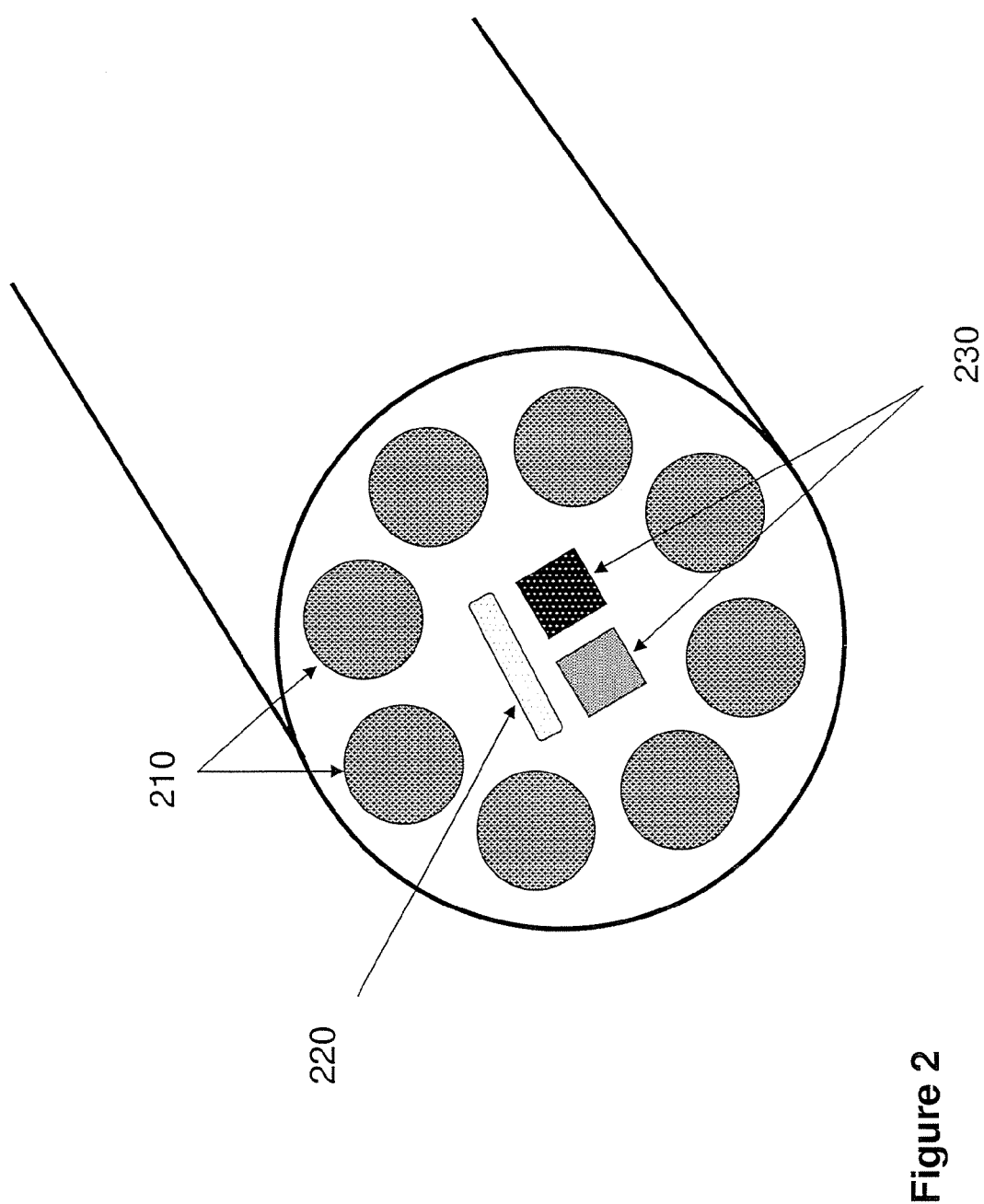
FIG. 2 provides a detailed view of the distal end of the device depicted in FIG. 1.

FIG. 2 shows a detailed embodiment of the distal end of the device, which includes the first light source (for example, blue LEDs or light emitting diodes 210, a detector such as a phototransistor 220, and a visible light source such as laser diodes 230; for example, a red diode and a green diode.

Figure 3:
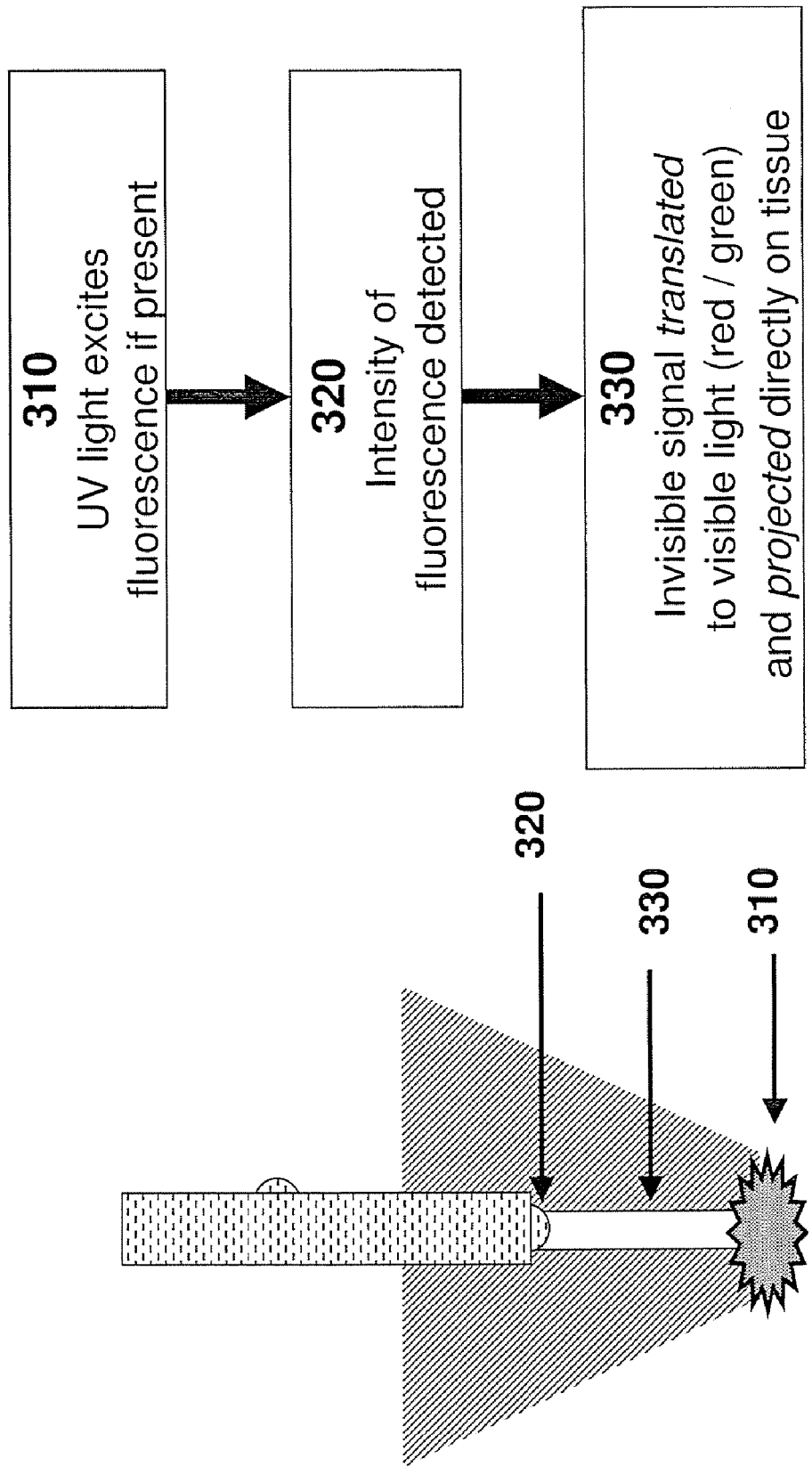
FIG. 3 provides a flow chart and diagram illustrating the function of the device in accordance with an embodiment of the invention.

FIG. 3 provides a diagram of the function of an embodiment of the hand-held device shown in FIGS. 1 and 2. The device in the form of a percutaneous device would also function in a similar manner. A first light source, for example an ultraviolet light source, is projected onto the region of interest 310, e.g., the surgical field in the area of the ureter or bile duct. If fluorescence is detected 320 which is above a threshold level by the light detector (e.g., a photodetector), a visible light is projected back onto the region of interest 330 (e.g., a red light from a red diode), indicating that the structure of interest is present in the region (e.g., a ureter). If no fluorescence is detected by the light detector, a visible light is also projected back onto the region of interest, however this projected light would be of a different color, e.g., from a green diode, indicating to the operator or surgeon that the structure of interest is not present in the region. If the amount of fluorescence detected is in-between zero and a predetermined threshold level, then the light projected back on to the region of interest can be of an intermediate color, e.g., orange, which represents a combination of the red and green diodes. The intermediate color can reflect whether the amount of fluorescence detected is closer to zero (e.g., a yellow light may be projected) or closer to a threshold amount (e.g., an orange light may be projected). The region of interest can be a "single data point"; by single data point is meant for example an area that may range from about 1 mm to 10 cm diameter, such as from 5 mm to 5 cm diameter and including from about 1 cm to 3 cm diameter.

Figure 4:
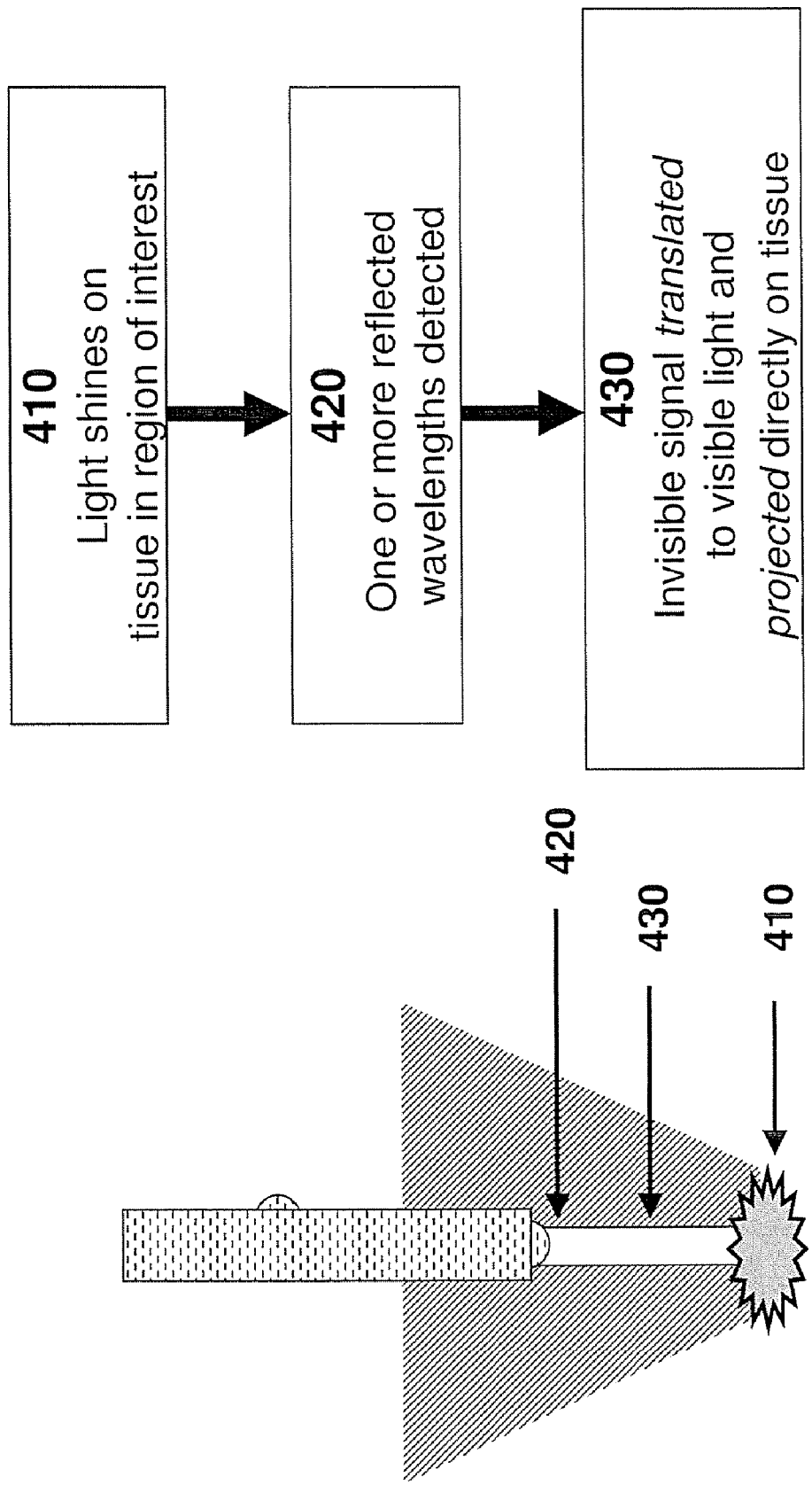
FIG. 4 provides a flow chart and diagram illustrating the function of the device in accordance with another embodiment of the invention.

FIG. 4 provides a diagram of the function of another embodiment of the hand-held device shown in FIGS. 1 and 2. A first light source, for example an light source suitable for optical intrinsic signal spectroscopy (OIS), is projected onto the region of interest 410, e.g., the surgical field in a region of the brain. If the reflected light detected 420 by the light detector (e.g., a photodetector) at one or more wavelengths of interest is above a threshold level, a visible light is projected back onto the region of interest 430 (e.g., a red light from a red diode). The color of this projected visible light can indicate that a particular level of oxygenation is present in the region. If the detected level of oxygenation, e.g., is below a particular level, a visible light is also projected back onto the region of interest, however this projected light would be of a different color, e.g., from a green diode, indicating to the operator or surgeon a different level of oxygenation in this region.

FIG. 5 provides an example showing use of the device to locate the ureter during surgery. A surgical field in the abdominal cavity 550 with the exposed ureter 540 is shown. A first light source, for example an ultraviolet light source, is projected onto the region of interest 510 e.g., the surgical field in the area of the ureter. If no fluorescence is detected 520, a visible light of a particular color (e.g., a green light from a green diode) is projected back onto the region of interest 530, indicating that the ureter is not present in the region. However, if a first light source is projected onto a region which contains the ureter 515, fluorescence above a threshold level 525 will be detected by the light detector (e.g., a photodetector). A visible light of a different color 535, e.g., red from a red diode, is then projected back onto the region of interest. The red color indicates to the operator or surgeon that the ureter is present.

Methods

The subject devices find use in methods in which a fluorescent agent is located in a portion of a body, which can be in an open surgical procedure or a biopsy, including of the skin or oral cavity, for example, or can be used with laparoscopic, or endoscopic procedures. As such, the subject devices can be used as a method for detecting a fluorescent agent in a portion of the body, or region of interest, comprising irradiating the portion of the body with light of a first wavelength, detecting light of a second wavelength emitted from the portion of the body, and emitting visible light onto the portion of the body from a visible light source that emits light having a color selected based on the amount of light detected at the second wavelength by the light detector. The subject methods are suited for use in "open" procedures, in which the device can be a hand-held device, or the subject devices can be used in minimally invasive or "non-open" surgical procedures in which a percutaneous device can be used, e.g., laparoscopic procedures.

By "fluorescent agent" is meant any agent that can absorb radiation at a first wavelength, and then emit radiation, usually at a different second wavelength, after exposure to external radiation, such as light or x-rays. In some embodiments the fluorescent agent can be administered to a patient, e.g., intravenous fluorescein, and in some embodiments, the fluorescent agent is an agent that is already present in the body, e.g., bile.

By "procedure" is meant any procedure, such as an "open" surgery, or a laparoscopic surgery, or a biopsy, such as a biopsy of the skin or oral cavity, or other procedures including but not limited to endoscopy of the gastrointestinal tract, endoscopic retrograde cholangiopancreatography (ERCP), duodenoscope-assisted cholangiopancreatoscopy, intraoperative cholangioscopy bronchoscopy, thorascopy, mediastinoscopy, laryngoscopy, rhinoscopy, otoscopy, ventriculoscopy, cystoscopy, hysteroscopy, colposcopy, arthroscopy, for example, or any procedure or surgery in which the location and position of an anatomical structure is of interest.

By "ambient light" is meant the background light incident upon a subject. For a subject on the operating room table, the ambient light includes at least room light, and may include also overhead lamps, the surgeons' headband-based lamps, and other light sources. Internally, ambient light can include light from an endoscope, laparoscope, bronchoscope, etc. or any other light associated with a percutaneous device.

The subject devices may be used to detect fluorescent agents in a body using a variety of different methods depending on the particular design of the device being employed. The subject methods can therefore be methods of locating an anatomical structure in the body during a procedure, such as surgery. The subject methods can further be methods of locating an anatomical structure in the body during a minimally invasive procedure, such as laparoscopic surgery or endoscopy. The subject methods can be used in procedures such as biopsies, for example of a surface lesion on the skin, or oral cavity, for example. The term "anatomical structure" is used broadly to refer to any type of object or structure in, near, or on the surface of the animal body. Representative structures that may be located employing the subject devices in the subject methods include: tissues, organs or parts thereof, such as ureters or bile ducts, internal vascular objects, e.g., vascular obstructions or lesions, tumors, and the like.

The subject devices can also be used to detect the properties of the optical signals from reflected light such as with optical intrinsic signal (OIS) mapping, using a variety of different methods depending on the particular design of the device being employed. The subject methods can therefore be methods of converting optical signal from a body tissue or body fluid, which can be invisible under normal ambient light conditions, to a clear visible signal which can be projected back onto the operative or therapeutic field. The subject methods can further be methods of determining a physiologic parameter, in which the processor is configured to operate as a "translator" of the one or more signals from the region of interest, which are not visually detectable, to a visible light which has a color reflecting the result of the calculated physiologic parameter, such as hemoglobin concentration or blood oxygenation. Physiological parameters that can be determined using the detected optical signal can include but are not limited to: hemoglobin concentration, blood oxygenation, blood flow, blood volume, blood glucose concentration, and cell swelling.

By "adjuvants" is meant a compound that, when used in combination with the one or more fluorescent agent compounds and/or compositions, augments or otherwise alters or modifies the resultant fluorescent and/or physiological responses.

A fluorescent agent of the subject methods can be a fluorescent agent that is naturally found in the body, e.g., bile porphyrins. A fluorescent agent can also be an agent that is administered, e.g., fluorescein, that can be administered to a subject in an amount effective to result in fluorescence of the anatomical structure of interest. By "effective amount" and analogous terms is meant a dosage sufficient to result in fluorescence of the anatomical structure of interest for a given period of time. The effective amount will vary with the age and physical condition of the subject, the anatomical structure of interest, the duration of the procedure, the nature of any concurrent treatment, the pharmaceutically acceptable carrier used if any, and analogous factors within the knowledge and expertise of those skilled in the art.

In certain embodiments, more than one fluorescent agent may be administered at the same or different time as another fluorescent agent to result in fluorescence of the anatomical structure of interest, where the pharmacological agents administered may differ in one or more respects, e.g., may be different types of agents or may be the same type fluorescent agent but one that differs in mode of administration, dosage, etc.

The effective amount of a given fluorescent agent may vary somewhat from subject to subject, and may depend upon factors such as, but not limited to, the age of the subject, the health of the subject, the anatomic structure of interest, the form of the fluorescent agent, the route and method of delivery, etc., as noted above. Such dosages may be determined in accordance with routine pharmacological procedures known to those skilled in the art. Fluorescent agents and/or adjuvants may be administered to a subject in one or more oral doses, for as long as necessary for the procedure of interest. The frequency of administration of a fluorescent agent may vary depending, e.g., on one or more of the factors described above. For example, the frequency of administration of a fluorescent agent may range from once before the procedure or surgery, to multiple times during the procedure or surgery, e.g., about 2 times or more or as necessary to continue to produce fluorescence for the duration of a procedure or surgery.

Fluorescent agents may be administered to a subject in a pre-active (pro-drug) form, followed by a bioactivation step in which the fluorescent agent requires activation through a biological interaction before producing, reducing, or altering its native signal. Such interactions include enzymatic processing, conformational changes, receptor binding, gene expression, and the like. For example, a conformational change can be the result of a pH change or of a binding event that swings fluorescence quenching groups into or out of position, decreasing or increasing the signal in response to binding. Similarly, an enzymatic processing may be an irreversible cleavage that removes fluorescence quenching moieties from the contrast agent, turning on a strong signal. Last, a bioinactivation step can be used to shut off the contrast in response to a biological event.

Depending on the particular fluorescent agent administered to a subject, the fluorescent agent may be administered to a subject using any convenient protocol capable of resulting in the desired fluorescence of the anatomical structure of interest. Administration protocols of interest include, but are not limited to: parenteral, oral, etc. As noted above, in pharmaceutical dosage forms, a given fluorescent agent may be administered alone or in appropriate association with, as well as in combination with, other fluorescent compounds. As used herein, "administered with" means that a given fluorescent agent and at least one other adjuvant (including one or more other different fluorescent agents) are administered at times sufficiently close that the results observed are indistinguishable from those achieved when the fluorescent agent and at least one other adjuvant are administered at the same point in time. The fluorescent agent and at least one other adjuvant may be administered simultaneously (i.e., concurrently) or sequentially. Simultaneous administration may be carried out by mixing a given fluorescent agent and at least one other adjuvant prior to administration, or by administering a given pharmacological agent and at least one other adjuvant at the same point in time. Such administration may be at different anatomic sites or using different routes of administration. The phrases "concurrent administration," "administration in combination," "simultaneous administration" or "administered simultaneously" may also be used interchangeably and mean that a given fluorescent agent and at least one other adjuvant are administered at the same point in time or immediately following one another. In the latter case, the fluorescent agent and at least one other adjuvant are administered at times sufficiently close that the results produced are synergistic and/or are indistinguishable from those achieved when the at least one fluorescent agent and at least one other adjuvant are administered at the same point in time. Alternatively, a fluorescent agent may be administered separately from the administration of an adjuvant, which may result in a synergistic effect or a separate effect.

A wide variety of different fluorescent agents may be employed in the practice of the subject methods, where the particular fluorescent agent or combination of fluorescent agents employed will depend on, e.g., the subject being treated, the type of procedure or surgery, the duration of the procedure or surgery, and the anatomic structure or structures of interest.

Suitable fluorescent agents that may be used in the subject methods include any non-toxic agent when exposed to radiant energy, e.g., light. In certain embodiments the dye is a fluorescent dye that emits light in the ultraviolet spectrum. In certain embodiments the dye is a fluorescent dye that emits light in the infra red spectrum. Suitable fluorescent agents can include but are not limited to fluorescein, quantom dots, fluorescein-based or fluorescent bile acids, e.g. cholylglycylaminofluorescein, or cholyllysylfluorescein, tissue specific lanthanide, terbium, europium or dysprosium chelates, chelating agents based upon tetraazamacrocyclic backbones, including aminocarboxylate and aminophosphonate chelating agents derived from 1,4,7,10-tetraazacyclododecane, macrocyclic lanthanide chelates, laser fluorescent dye derivatives, polyaminopolyacetic acid derivatives conjugated with an electroluminescent moiety, rhodamine, phycoerythrin, phycocyanin, allophycocyanin, o-phthaldehyde, fluorescamine, fluorescein isothiocyanate rose Bengal, trypan blue, fluorogold, indocyanine green, or any suitable fluorescent agent as is known in the art. The aforementioned agents may be mixed or combined in certain embodiments. In some embodiments fluorescent agent analogs may be used. A fluorescent agent analog includes a fluorescent agent that has been chemically modified, but still retains its ability to fluoresce when exposed to radiant energy of an appropriate wavelength. Fluorescent agents can be agents that are naturally occurring in the body, such as bile, or porphyrins, for example.

In some embodiments, intravenous fluorescein can be used as the fluorescent agent. In human pharmacologic studies of fluorescein, 80% of a 14 mg/kg dose was metabolized within 1 hour of IV administration. Elimination of fluorescein and its metabolites occurs mainly through renal excretion, with a renal clearance rate estimated at 1.75 ml/min/kg. The urine remains slightly fluorescent for 24-36 hours post dose. The volume of distribution is 0.5 L/kg, and thus 0.05 mg/min of drug will be excreted into the ureters. A normal rate of urine production is on the order of 0.5 ml/min, and so the concentration of fluorescein in urine would be about 0.1 mg/ml, or about 5× the concentration of fluorescein in the blood.

For example, the device can be used to locate the ureters in a pelvic surgery in which location of the ureters is desired, in order to avoid injury to the ureters. Surgeries of interest in which damage to the ureter is a risk, include but are not limited to: hysterectomies, adnexal surgeries, colorectal surgeries, incontinence surgery, and vascular surgeries. Additional procedures can include complex pelvic surgeries such as with cancer surgeries, and tumor detection, etc. A fluorescent agent, e.g., intravenous fluorescein, can be injected. Once the fluorescein reaches the kidneys and is excreted into the ureters, a hand-held device can be used either by the surgeon, nurse, or other operating room assistant. The device can be aimed at any area within the surgical field. The device is activated, and a collimated light of a first wavelength, e.g., an ultraviolet light source, can be projected onto the region of interest in the surgical field. A light detector, e.g., a phototransistor behind one or more optical filters is then used to assess the intensity of any fluorescence. If the device is initially directed away from the ureters, little or no fluorescence will be detected. In the case in which visible light is provided by red and green diodes, for example, the visible light projected back onto the operative field will be green, indicating to the surgeon that there is no danger of injury to the ureters in that region of interest. If a relatively higher concentration of fluorescence is detected, implying the presence of the ureter, a collimated red light is emitted onto the scanned area. When the visible light projected back onto the operative field is red, it can indicate to the surgeon that the ureter in present in the region of interest, which can assist the surgeon in avoiding inadvertent injury to the ureter. In this way, the subject device translates the fluorescence signal, invisible under normal conditions, to a clear visible signal. If the visible light projected back onto the operative field is orange, for example, it can indicate to the surgeon that the ureter is close, and to proceed with caution to avoid injury to the ureter. The subject device and methods can be used to locate ureters, for example, not only to avoid injury to the ureters, but also to locate them, especially if there has been previous surgery in the region and the anatomy is distorted. To locate the ureters, a "scanning" process is used, in which the surgeon moves the device over an extended region of the surgical field, and s/he can see the projected light turn from green to orange to red as the ureters are located.

The device can also be used to convert an "invisible" optical signal to a visible optical signal e.g., during an operation or procedure in the brain. The device can be aimed at any area within the surgical field. The device is activated, and a first light source, e.g., a white light source, can be projected onto the region of interest in the surgical field. A light detector, e.g., a phototransistor behind one or more optical filters is then used to detect the reflected wavelength or wavelengths of interest. The processor can then convert the one or more signals from the region of interest, which are not visually detectable to the unaided human eye, to a visible light which has a color reflecting the result of the calculated physiologic parameter, such as hemoglobin concentration or blood oxygenation. In the case in which visible light is provided by red and green diodes, for example, the visible light projected back onto the operative field can be green, for example, if the blood oxygenation level is above a desired threshold. If a relatively lower oxygenation level is detected, for example, a collimated red light can be emitted onto the scanned area. In this way, the subject device translates the optical signal, invisible under normal conditions, to a clear visible signal.

Two differently-colored diodes are provided in the subject device for multiple reasons. First, it is important to provide a projected signal regardless of whether fluorescence is detected or not, in order to assure the user of proper device operation. For example, a green cue can ensure that surgeons are alerted not only when the ureter is dangerously near, but also when they are likely to be clear of potential ureteral injury.

The two different diodes will also allow the user to assess proximity to the fluorescing material, and thus while manipulating the device the user can quickly identify the ureters by attempting to maximize the "red" pointer. Either varying duty cycle or current can control the perceived intensity of each laser diode. In the case of duty cycle, when the sensor detects a low intensity of fluorescence, the duty cycle of the green diode would increase, while that of the red diode would decrease, and the user would perceive a green pointer. When the sensor detects a high intensity of fluorescence, the duty cycle of the red diode would likewise increase. Thus, when moving the pen from an area far from the ureter to directly over the fluorescing ureter, the user will see the output color transition from green, to greenish-orange, to reddish-orange, to red.

In a similar manner, the device can be used to locate the bile ducts in a laparoscopic abdominal surgery in which locating of the bile ducts is desired, in order to avoid injury to the ducts. A percutaneous device which has been placed into a subject through a port can be used either by the surgeon, nurse, or other operating room assistant. The device can be aimed at any area within the surgical field. The device is activated, and a collimated first light source, e.g., with a peak wavelength of 475 nm can be projected onto the region of interest in the surgical field. If a fluorescent substance such as bile is present in the region illuminated by the collimated light source, then fluorescence at least one wavelength, e.g., 480 nm, will be emitted from the fluorescent substance and can be detected by at least one detector on the device. If the device is initially directed away from the bile ducts, no fluorescence will be detected, and in the case in which visible light is provided by red and green diodes, for example, the visible light projected back onto the operative field will be green, indicating to the surgeon that there is no danger of injury to the bile ducts in that region. Because of the autofluorescent properties of bile, which has an excitation wavelength of about 475 nm, if the device is directed toward the bile ducts the resulting fluorescence will be detected, and the visible light projected back onto the operative field will be red. This can indicate to the surgeon that the is one or more bile ducts are present in the region of interest. The surgeon can then avoid inadvertent injury to the ducts. If the visible light projected back onto the operative field is orange, for example, it can indicate to the surgeon that a bile duct is only partially within the region illuminated by the device, and to proceed with caution to avoid injury to the ducts. The subject device and methods can be used to both avoid bile ducts, and also to assist in locating them, especially if cases where there has been previous surgery in the region and the anatomy is distorted.

Kits

Also provided are kits that at least include the subject devices. The subject kits at least include a device of the subject invention and instructions for how to use the device in a procedure. The kit can also include a fluorescent agent, e.g., fluorescein. The device provided in the kit can be a hand-held device, or can be a percutaneous device.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g., CD-ROM, diskette, etc. The instructions may take any form, including complete instructions for how to use the device or as a website address with which instructions posted on the world wide web may be accessed.

The following example is offered by way of illustration and not by way of limitation.

EXPERIMENTAL

Evaluation of the Fluorescent Signal

The feasibility of detecting the fluorescent signal through the wall of the ureters was evaluated using a porcine model. A laparotomy was performed on a euthanized pig and the ureter was dissected out from the retroperitoneum. The proximal ureter was catheterized and injected with 0.25%, 0.5%, and 1.0% concentrations of fluorescein. Background fluorescence was simulated by washing the peritoneum with fluorescein. Under a Woods lamp (standard surgical black light) with the room lights off, the ureter was highlighted well for each concentration administered. As expected, with the room lights on, the fluorescent signal became dim and nearly impossible to see.

This procedure was repeated on the contralateral intact ureter, again simulating background fluorescence by staining the peritoneum. The ureters were well-visualized at all concentrations of fluorescein administered.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device comprising:
   a first light source configured to emit light onto a region of interest in a subject's body;
   a light detector configured to detect light reflected from said region of interest;
   a processor configured to convert the amount of detected light from said light detector into outputs representative of a blend of visible light of a particular color that is to be projected back onto said region of interest, said color being indicative of the proximity of said device to an anatomical structure within said region of interest, and
   a second and a third light source responsive to said outputs and configured to emit said visible light of a particular color onto said region of interest, said visible light having a color that is a color blend of the colors of said second and third light sources which indicates the proximity to said device.

2. The device according to claim 1, wherein said visible light sources comprise a first diode and a second diode.

3. The device according to claim 2, wherein said first diode emits light at a wavelength that ranges from 495 to 570 nanometers.

4. The device according to claim 2, wherein said second diode emits light at a wavelength that ranges from 620 to 750 nanometers.

5. The device according to claim 1, wherein said first light source is a collimated light source.

6. The device according to claim 1, wherein said first light source emits light at a first wavelength that ranges from 350 to 495 nanometers.

7. The device according to claim 1, wherein said second light has a color ranging from green to red.

8. The device according to claim 1, wherein said light detector detects light at a wavelength that ranges from 500 to 530 nm.

9. The device according to claim 1, wherein said device is a hand-held device.

10. The device according to claim 1, wherein said device is a percutaneous device.

11. A method of detecting a fluorescent agent in a portion of a subject's body, said method comprising:
    irradiating said portion of said body with light of a first wavelength from a first light source;
    detecting light of a second wavelength emitted from a fluorescent agent present in said portion;
    converting the amount of detected light into outputs representative of a blend of visible light of a particular color, said color being indicative of the proximity of said device to an anatomical structure within said portion;
    emitting visible light onto said portion from a second and a third light source responsive to said outputs wherein said visible light of a particular color is a blend of the colors of the second and third light sources, said color indicating the proximity to said device.

12. The method according to claim 11, wherein said visible light sources comprise a first diode and a second diode.

13. The method according to claim 12, wherein said first diode emits light at a wavelength that ranges from 495 to 570 nanometers.

14. The method according to claim 12, wherein said second diode emits light at a wavelength that ranges from 620 to 750 nanometers.

15. The method according to claim 11, wherein said light of a first wavelength is a collimated light.

16. The method according to claim 11, wherein said first wavelength ranges from 350 to 495 nanometers.

17. The method according to claim 11, wherein said visible light has a color ranging from green to red.

18. The method according to claim 11, wherein said method further comprises administering said fluorescent agent to said body.

19. The method according to claim 11, wherein said method is a method of locating an anatomical structure.

20. The method according to claim 19, wherein said anatomical structure is a ureter.

21. The method according to claim 19, wherein said anatomical structure is a bile duct.

22. A kit comprising:
(a) a device comprising:
  (i) a first light source configured to emit light onto a region of interest in a subject's body;
  (ii) a light detector configured to detect light reflected from said region of interest;
  (iii) a processor configured to convert the amount of detected light from said light detector into outputs representative of a blend of visible light of a particular color that is to be projected back onto said region of interest, said color being indicative of the proximity of said device to an anatomical structure within said region of interest; and
  (iv) a second and a third light source responsive to said outputs and configured to emit said visible light of a particular color onto said region of interest, said visible light having a color that is a color blend of the colors of said second and third light sources which indicates the proximity to said device; and
(b) a fluorescent agent.

* * * * *